United States Patent
Rodriguez

(12) 
(10) Patent No.: US 6,821,997 B1
(45) Date of Patent: Nov. 23, 2004

(54) THERAPEUTIC AND PROPHYLACTIC TREATMENT OF AGING AND DISORDERS OF AGING IN HUMANS

(76) Inventor: Victorio C. Rodriguez, 7791 Hoertz Rd., Parma, OH (US) 44134

( * ) Notice: Subject to any disclaimer, the term of this patent is extended or adjusted under 35 U.S.C. 154(b) by 121 days.

(21) Appl. No.: 10/077,719

(22) Filed: Feb. 15, 2002

Related U.S. Application Data

(63) Continuation-in-part of application No. 09/688,290, filed on Oct. 16, 2000, now abandoned.

(51) Int. Cl.$^7$ ............................................. A61K 31/417
(52) U.S. Cl. ........................ 514/400; 514/396; 514/397; 514/398; 514/399; 514/878; 514/879
(58) Field of Search ................................ 514/400, 396, 514/397, 398, 399, 878, 879

(56) References Cited

U.S. PATENT DOCUMENTS 5,972,684 A 10/1999 Bandman et al.
6,552,053 B2 * 4/2003 Sun et al. .................... 514/363

FOREIGN PATENT DOCUMENTS

EP 680960 * 11/1995

OTHER PUBLICATIONS

Brown, D., "Estrogen study on Monopausal women is stopped," Washington Post, Mar. 3, 2004, pg. A2.*
File CAPLUS on STN, Chemical Abstracts Service, Columbus, Ohio, accession No. 2004: 148096, 2004.*
MEDLINE abstract, accession No. 2003399581, 2003.*
Chemical Abstracts 139: 173705, 2003.*
Chemical Abstracts 124:83843,1995.*
Chemical Abstracts 110:152187, 1989.*
Tozer, Matthew J. et al. "4–chlorobenzyl sulfonamide and sulfamide derivatives of histamine homologues: the design of potent histamine H3 receptor antagonists," Bioorganic & Medicinal Chemistry Letters, vol. 9 (21), 1999, pp. 3103–3108.*
Medline Abstract, accession No. 1999441621 (1999).*
Reichlmeier K, Ermini M, Schlecht H.P., "[Age–dependent enzymatic changes in human cerebral cortex (author's transl)]" [Article in German], Aktuelle Gerontol 1978 Aug:8(8):441–8—ABSTRACT ONLY.
Meier_Ruge, W., Iwangoff, P., Reichlmeier, K., and Sandoz, P., "Neurochemical findings in the Aging Brain" Adv. Biochem Psychopharmacology 1980;23;323_38—ABSTRACT ONLY.

Cabisco, E. and Levine, R. L., "Carbonic anhydrase III. Oxidative modification in vivo and loss of phosphatase activity during aging", J. Biol. Chem.1995 Jun. 16;270(24):14742–7—ABSTRACT ONLY.

Huang W, Smith Se, Chesler M., "Addition of carbonic anhydrase augments extracellular pH buffering in rat cerebral cortex.", J. Neurophysiol 1995 Oct;74(4): 1806–9—ABSTRACT ONLY.

Boren K, Freskgard PO, Carlsson U., "A comparative CD study of carbonic anhydrase isoenzymes with different number of tryptophans: impact on calculation of secondary structure content.", Protein Sci 1996 Dec;5(12):2479–84—ABSTRACT ONLY.

Puscas I, Coltau M, Pasca R. "Nonsteroidal anti–inflammatory drugs activate carbonic anhydrase by a direct mechanism of action." J Pharmacol Exp Ther 1996 Jun;277(3):1464–6—ABSTRACT ONLY.

Henkin, R.I., Martin, B.M., and Agarwal, R. P., "Efficacy of exogenous oral zinc in treatment of patients with carbonic anhydrase VI deficiency", Am J Med Sci 1999 Dec;318(6):392–405—ABSTRACT ONLY.

Chaif, Truong_Tran Aq. Evdokiou A, Young GP, Zalewski PD., "Intracellular zinc depletion induces caspase activation and p21 Waf1/Cip1 cleavage in human epithelial cell lines.", J Infect Dis 2000 Sep;182 Suppl 1:S85_92_ABSTRACT ONLY.

* cited by examiner

Primary Examiner—John Pak
(74) Attorney, Agent, or Firm—Calfee, Halter & Griswold LLP

(57) ABSTRACT

A method for the treatment and prophylaxis of conditions of aging in humans, such conditions of aging associated with a decreased presence of cell-specific carbonic anhydrase enzymes in the brain, such as conditions associated with chronic neurodegenerative conditions including dementia such as Alzheimer's disease, which method includes the administering over an extended period of time, ranging from 6 months to 5 years, of a pharmaceutically effective, non-toxic amount of a compound that increases the presence of cell-specific carbonic anhydrase enzymes in the brain. That compound may be the cell-specific carbonic anhydrase enzyme, a compound that when absorbed by the body reacts or dissociates to form the cell-specific carbonic anhydrase enzyme, or a compound that promotes the natural generation of the cell-specific carbonic anhydrase enzyme within the body.

9 Claims, 1 Drawing Sheet

PATHOPHYSIOLOGY OF ALZHEIMER'S DISEASE AND OTHER NEURODEGENERATIVE DISORDERS

A. Primary deficiency of cell-specific carbonic anhydrase enzyme due to defective gene-link carbonic anhydrase enzymes
B. Secondary deficiency of cell-specific carbonic anhydrase enzyme due to:
   1. Neurotoxic materials, such as aluminum, iron, and lead
   2. Infections that alter the blood-brain barrier
   3. Amyloid deposits that alter the blood-brain barrier
   4. Other conditions or diseases that alter the blood-brain barrier that displace the zinc from cell-specific carbonic anhydrase enzymes

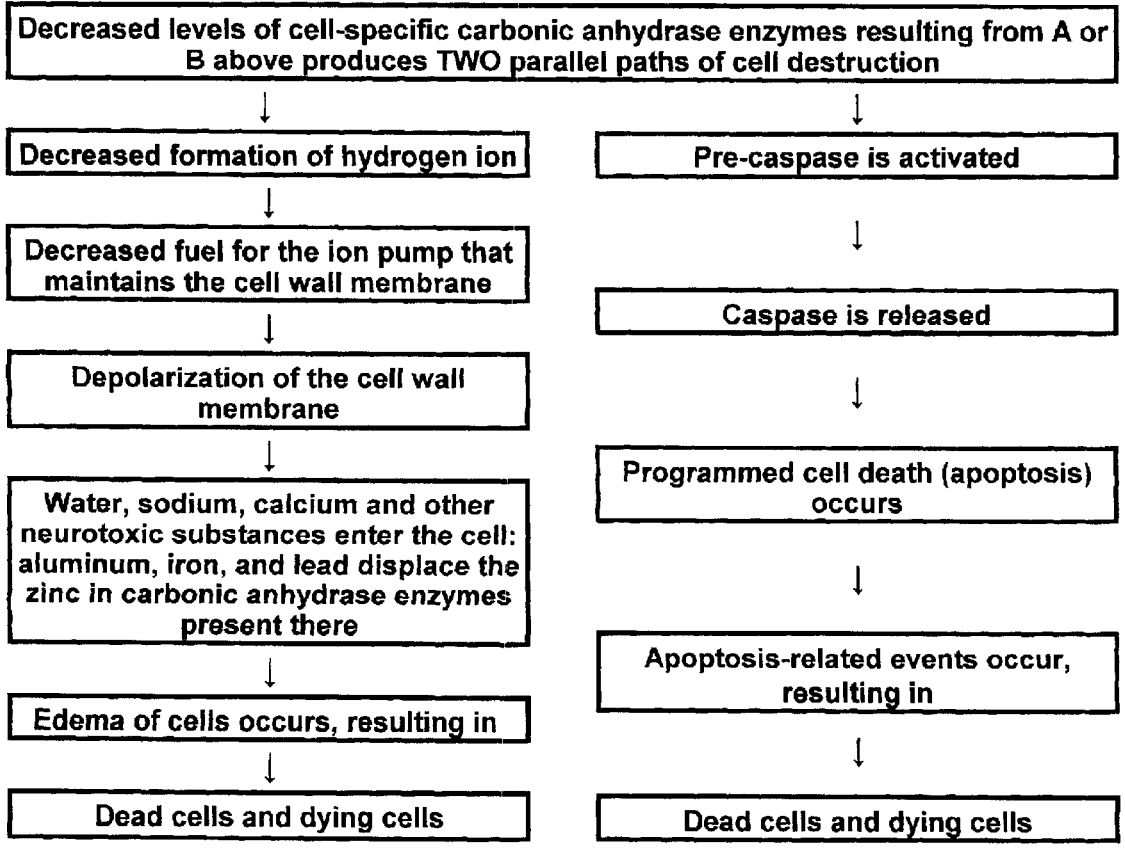

—— DEAD AND DYING CELLS INCLUDE NEURONS (BRAIN CELLS) ——
(Neuro-fibrillary tangles and tau proteins)

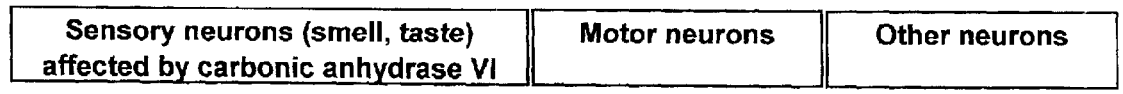

Fig. 1

THERAPEUTIC AND PROPHYLACTIC TREATMENT OF AGING AND DISORDERS OF AGING IN HUMANS

This application is a CIP of 09/688,290, filed on Oct. 16, 2000, now abandoned.

FIELD OF THE INVENTION

This invention deals with therapeutic and prophylactic treatment of age-related problems with humans. More specifically, a new use for existing medicaments that will counteract the aging process on a cellular level—particularly in the brain—is disclosed.

BACKGROUND

Normal aging in humans is recognized as producing some or all of the following typical physiological results:

1. Brain weight is reduced by 15%
2. Blood flow to the brain is reduced by 20%
3. Body water content is reduced by 18%
4. Body weight is reduced by 12%
5. Nerve conduction velocity is reduced by 10%
6. Number of nerve fibers in nerves are reduced by 37%
7. Decreased amounts of enzymes and coenzymes
8. Decreased amounts of neurotransmitters
9. Depletion of oxidative, phospohorelative enzymes
10. Apoptosis—chronic neuronal atrophy In describing their work in an article entitled "Studies on Age-Dependent Ozonide Changes in Human Cerebral Cortex," (by Reichlmeier K., Ermini M., and Schlecht H. P.—*Aktuelle Gerontol* 1978 August, 8(8):44–8), the authors report that they investigated the activity of various enzymes of human brains obtained at autopsy and covering an age range from 19 to 91 years. Protein kinase, which mediates the information carried by the second messenger, cyclic AMP (3',5'-cyclic adenosine monophosphate), does not show age-related changes of basal activity. Cyclic AMP-dependent activation of protein kinase remains nearly constant up to 60 years of life, but it undergoes a distinct and progressive decline between 60 and 90 years. In the corpus striatum, no age related changes of cyclic AMP-dependent protein kinase activity were observed. The activity of carbonic anhydrase exhibits, in both human cortex and corpus striatum, an age-dependent decrease that also begins after the sixth decade of life. These neurochemical changes may well be related to morphological and physiological changes occurring in the aging brain. They begin after the 60th year of life.

The following represents an essential chemical reaction that takes place in human tissue:

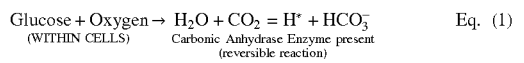

$$\text{Glucose + Oxygen} \rightarrow H_2O + CO_2 = H^+ + HCO_3^- \quad \text{Eq. (1)}$$
(WITHIN CELLS)  Carbonic Anhydrase Enzyme present
(reversible reaction)

Glucose is irreversibly oxidized within the cells to produce water and carbon dioxide. In the presence of a catalyst, especially a carbonic anhydrase enzyme (of which several forms exist, of which the form present depends upon the type of tissue cells present), the water and carbon dioxide reversibly produce a hydrogen ion and a bicarbonate ion.

Carbonic anhydrase is a zinc-containing enzyme-that catalyzes-the reversible $CO_2$ hydration reaction illustrated in Eq. 1. The mitochondria of cells of different tissues and organs produces different specific carbonic anhydrase enzymes that maintain the equilibrium of the above equation in all spaces—cellular, interstitial, and vascular—as illustrated in FIG. 1. At least seven carbonic anhydrase variants, called "isozymes" have been identified. The literature may refer to these as "carbonic anhydrases I through VII" or "CAS I–VII". We here refer to this selectivity as "cell-specific" and the particular carbonic anhydrase isozyme present as being a "cell-specific carbonic anhydrase enzyme."

Hydrogen ion produced by carbonic anhydrase enzymes is acted upon by cytochrome system, which is then utilized as the energy source of the ion pump that maintains the integrity of the cell membrane comprising and enclosing each cell. It is also thought to be a source of the brain's electric current. This process is schematically illustrated in FIG. 1, presented here with no further discussion.

Disruption of the process that includes Eq. 1 causes depolarization of the cell wall membrane, hence sodium (Na), water ($H_2O$), and other chemicals can enter the cell in uncontrolled amounts and potassium (K) can exit uncontrollably, leading to the death and destruction of the involved cells; cellular edema follows. As this edema progresses, the cell dies. Along with the progressive and gradual death of cells, gliosis follows—hence aging in the brain occurs.

In aging, there has been observed a progressive decrease in levels of enzymes of which carbonic anhydrase enzyme is one. Authors W. Meier-Ruge, P. Iwangoff, K. Reichlmeier, and P. Sandoz, in "Neurochemical findings in the Aging Brain (Adv. Biochem Psychopharmacology 1980;23;323–38) include carbonic anhydrase in their studies of normal aging on enzymes in the human brain cortex and putamen. Their study shows carbonic anhydrase, which they cites as being important to the regulation of the $pO_2/pCO_2$ ratio in the brain tissue, demonstrates a significant decline with increasing age. Thus, $pCO_2$-dependent regulation of tissue pH, ionic transport processes, and cerebral blood flow regulation have the tendency to become more and more unstable, they observe.

Authors E. Cabisco and R. L. Levine, in "Carbonic anhydrase III. Oxidative modification in vivo and loss of phosphatase activity during aging" (J. Biol. Chem. 1995 June 16;270(24): 14742–7), describe their utilizing an immunochemical method for detection of oxidatively-modified proteins, through which method they identified a protein in rat liver that was highly oxidized. It was purified to homogeneity and identified as carbonic anhydrase isozyme III. Its characteristics match those previously described for protein that was lost during aging of the rat, senescence marker protein-1. In their experiments, carbonic anhydrase III was purified from rats aged 2, 10, and 18 months and the proteins were characterized. All three preparations were highly oxidative modified, as assessed by their carbonyl content. The enzyme (carbonic anhydrase III) has three known catalytic activities, and the specific activities for carbon dioxide hydration and for ester hydrolysis decreased during aging by approximately 30%. However, the third activity, that of a phosphatase, was virtually lost during aging. While the physiologic role of carbonic anhydrase III is unknown, these authors suggest that it functions as an oxidizing environment, which leads to its own oxidative modification.

PRIOR ART

Carbonic anhydrase enzyme has been used to augment the extracellular pH buffering in the cerebral cortex of rats (*Journal of Neurophysiology* 1995 October '74(4):1806–9). It is known that the blood-brain barrier in animals is incomplete compared to that of humans where the blood-brain barrier is complete and a formidable barrier to chemical transport. Substances that prove efficacious in affecting the brain chemistry of animals are not necessarily efficacious in the brains of human beings because they cannot pass through the more complete blood-brain barrier in humans. Carbonic anhydrase enzymes appear to traverse the blood-brain barrier in humans. Although some researchers equivocate on this concept, most of the medical community accepts the idea that carbonic anhydrease enzymes traverse the blood-brain barrier in humans as fact, especially regarding the carbonic anhydrase enzyme referred to as CA-II.

As far as can be determined from the literature, cell-specific carbonic anhydrase enzymes have never been used to restore to a higher level the carbonic anhydrase enzymes that are lacking due to decreased levels due to normal aging. At least some of the carbonic anhydrase isozymes have been extracted from animal tissue, isolated, and studied for molecular structure. This shows that the enzymes can be isolated and made available for administration to a patient for therapeutic or prophylactic-treatment.

In U.S. Pat No. 5,972,684, Bandman et al. tell us:

"Eight enzymatic and evolutionarily related forms of carbonic anhydrase are currently known to exist in humans: three cytosolic isozymes (CAI, CAII, and CAIII, two membrane-bound forms (CAIV and CAVII), a mitochondrial form (CAV), a secreted salivary form (CAVI) and a yet uncharacterized isozyme. Isoforms show a characteristic motif. (See, e.g., http//expasy.hcuge.ch). Though the isoenzymes CAI, CAII, and bovine CAIII have similar secondary structure and polypeptide-chain fold, CAI has 6 tryptophans, CAII has 7 and CAIII has 8 (Boren, K. et al. (1996) Protein Sci. 5(12):2479–2484). CAII is the predominant CA isoenzyme in the brain of mammals."

"Inhibition and activation of CA provide information about CA stricture and activity. Vasodilating prostaglandins E1, E2 and I2 inhibit CA in vitro and in vivo and may inhibit the involvement of CA in gastric acid secretion. Nonsteroidal anti-inflammattory drugs which reduce the activity of cyclooxygenase and prostaglandin production have also been observed to activate CAI and CAII in a dose-dependent noncompetitive manner. The pre-prostaglandin cyclooxygenase appears to maintain an inverse relationship with CA, probably mediated by the pH variations associated with carbonic anhydrase activity (Puscas, I. (1996) J. Pharmacol. Exp. Ther. 277(3):1464–1466). Both prostaglandins E2 and I2 inhibit gastric acid output. Prostaglandin. E2 inhibits egress of norepinephrine from sympathetic nerve terminals."

The Bandman et al. patent teaches another carbonic anhydrase, CA-VIII, the subject of their patent. The present patent does not deal with nor address CA-VIII.

Patients having a carbonic anhydrase VI (CA-VI) deficiency have been treated with orally-administered zinc in an effort to stimulate the synthesis/secretion of CA-VI and the successful results were reported in the American Journal of Medical Science (Efficacy of exogenous oral zinc in treatment of patients with carbonic anhydrase VI deficiency, by Henkin, R. I., Martin, B. M., and Agarwal, R. P.—Am J Med Sci 1999 December;318(6):392–405). Thus, it is shown-that the synthesis/secretion of carbonic anhydrase can, indeed, be stimulated by compounds administered orally.

BRIEF DESCRIPTION OF THE DRAWINGS

FIG. 1 illustrates the pathophysiology of neurodegenerative disorders.

DESCRIPTION OF THE BEST MODE

Referring to FIG. 1, we observe two parallel paths of cell destruction that can be directly linked to deficiencies of cell-specific carbonic anhydrase enzymes, whether the decreased level of CA is a primary deficiency or a secondary deficiency, as described therein. One path relates to the breakdown of the chemical reaction shown in Eq. 1 and the other relates to the release of caspase, leading to apoptosis. The result of both paths is dead cells and dying cells, which include brain cells and other neural cells. Here we show that at least one cause of the destruction of brain cells and other neurons is traceable to decreased levels of cell-specific carbonic anhydrase enzymes.

Heretofore, researchers had identified only one of these parallel paths, the one involving caspase. Specifically, it has been reported in the Journal of Infectious Diseases, 2000 September;182 Suppl 1:S85–92, by F. Chai, et al. that the mechanism by which zinc deficiency (equivalent to deficiency in zinc-carrying carbonic anhydrase enzyme) induces epithelial cell death involves the activation of caspase-3 as indicated on the right half of FIG. 1. The suggestion is made from this research that zinc (i.e., CA) may suppress a step just before the activation of the caspase and a zinc (i.e., CA) deficiency results in a failure to suppress that step.

The path illustrated on the left half of FIG. 1 is newly presented in the instant invention. The decreased levels of CA (i.e., zinc-carrying enzyme) upset the rate of the reversible portion of the reaction indicated in Eq. 1, above, decreasing the formation of hydrogen ion that is the fuel for the ion pump that maintains the cell wall membrane, leading to depolarization and allowing neurotoxic substances to enter the cell, causing edema and cell death.

Whereas in aging, there has been observed a progressive decrease in levels of enzymes of which carbonic anhydrase enzyme is one, I believe that replenishing the carbonic anhydrase enzymes that catalyze the reversible reaction portion of Equation 1 will at least slow the progressive and gradual death of cells, including cells in the brain, which brain cell reduction is a major contributor to various brain disorders involving dementia such as Alzheimer's disease, and neurodegenerative diseases.

Cell-specific carbonic anhydrase enzymes have never been used to restore to a higher level the carbonic anhydrase enzymes that are lacking due to decreased levels due to normal aging, whether the replenishing enzymes are naturally produced and harvested or synthetically produced, nor has anyone used for this purpose any carbonic anhydrase stimulators to stimulate a patient's production of carbonic anhydrase enzymes.

I have come to the realization that administering supplemental cell-specific carbonic anhydrase enzymes or administering cell-specific carbonic anhydrase enzyme stimulators, the effects of aging, especially in the central nervous system, by raising the level of cell-specific carbonic anhydrase enzymes present. In using the term "stimulators" I mean to include materials for stimulating the production of cell-specific carbonic anhydrase enzymes. Another method for raising the level of the required enzymes is to directly administer the enzymes themselves. These enzymes can be naturally-produced enzymes or synthetically-produced enzymes. Means and techniques are available in the medical literature for extracting naturally-produced enzymes.

This treatment can be administered to patients exhibiting signs of Alzheimer's disease or showing other forms of dementia or neurodegenerative diseases. It is also feasible to administer this treatment as a prophylactic or preventative to an aging patient to prevent or at least delay the onset of such dementia, from whatever cause.

Thus, I disclose here a method for the treatment and prophylaxis of conditions of aging associated with a decreased presence of cell-specific carbonic anhydrase enzymes in the brain, such as conditions associated with chronic neurodegenerative conditions including dementia such as Alzheimer's disease, which method comprises the administration over an extended period of time in the range of six months to five years, of a pharmaceutically effective, non-toxic amount of a compound that increases the presence of a cell-specific carbonic anhydrase enzymes in the brain. The carbonic anhydrase enzyme found most abundantly in the brain is referred to as CA-II; the method may be applied to other carbonic anhydrase enzymes as well as to CA-II.

The compound used could be the cell-specific enzyme that is believed to be evidencing a decreased presence as measured in blood tests or in cell cultures of brain cells from biopsied tissues or from cerebro-spinal fluid. Alternatively, the compound used could be synthetically produced cell-specific carbonic anhydrase enzyme. As another alternative, the compound used could be naturally-produced cell-specific carbonic anhydrase enzyme. Yet another alternative allows that the compound used is a compound that, when administered to a human patient will promote the natural production of the cell-specific enzyme that is evidencing a decreased presence as measured in blood tests or in cell cultures of brain cells from biopsied tissues or from cerebro-spinal fluid. The compound itself need not be one that passes the blood-brain barrier; the cell-specific enzyme need not be produced within the brain for it is known to pass the blood-brain barrier so the promoting of the natural production of the cell-specific enzyme can take place elsewhere in the body.

Examples of compounds that are known to promote the natural production of the required cell-specific enzyme comprise: zinc; sex hormones, androgen and estrogen; certain non-steroidal anti-inflammatory drugs, including indomethacin; 1,25-dihydroxyvitamin D3; phorbol myristate acetate; cysteamine; and certain sufonylamido derivatives of histamine. For instance, the sex hormones androgen and estrogen are known to increase the production of carbonic anhydrase III. Vitamin D3 increases the production of carbonic anhydrase II.

Administering the compound may be done by injection or ingestion. The injection method used may be intramuscular or intravenous, dissolved in a sterile saline solution, glucose solution, or other commonly-administered parenteral solution. The best method of administering the compound will be learned with modest experimentation. The individual patient's response to the compound will be learned through testing for the cell-specific enzyme in blood samples taken before and after administering the medication and by enzyme levels measured from cell cultures of brain cells from biopsied tissues or found in cerebro-spinal fluid. The goal is to increase the level of the cell-specific enzyme in the brain from its reduced level to a more normal level. Insofar as the enzyme level in the blood is a reflection of the enzyme level in the brain, the blood tests may be a sufficient indicator. In addition, and other means of measuring enzyme levels that are known to the practitioner may be employed.

Pharmaceutical compositions suitable for use in the invention include compositions wherein the active ingredients are contained in an effective amount to achieve the intended purpose. The determination of an effective dose is well within the capability of those skilled in the art.

A therapeutically effective dose refers to that amount of active ingredient that ameliorates the symptoms or condition, the condition being caused by or reflected in reduced concentration of carbonic anhydrase. Therapeutic efficacy and toxicity may be determined by standard procedures from blood testing, from biopsied tissues, and by other means known to the practitioner, for comparison with the normal values. The dosage is preferably within a range of circulating concentrations that are efficacious with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect, which is a near-normal level of the cell-specific enzyme. Factors which may be taken into account include the severity of the enzyme reduction extant in the subject, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 grain, depending upon the route of administration. Guidance as to particular dosages and methods of delivery is provided in the literature and generally available to practitioners in the art. Those skilled in the art will employ different formulations to achieve the desired results.

I claim:

1. A method for the treatment and prophylaxis of conditions of aging associated with a decreased presence of cell-specific carbonic anhydrase enzymes in the brain, such as conditions associated with chronic neurodegenerative conditions including dementias such as Alzheimer's disease, which method comprises identifying which one or more cell-specific carbonic anhydrase enzymes are present at decreased levels in the blood or brain cells of a subject; and then administering a pharmaceutically effective, non-toxic amount of a compound that increases the presence of said cell-specific carbonic anydrase enzymes in the blood or brain cells of the subject.

2. The method of claim 1 wherein said compound is a compound that, when administered to a human patient will promote the natural production of the cell-specific enzyme that is present at decreased levels in the subject.

3. The method of claim 1 wherein said administering is by injection.

4. The method of claim 3 wherein injection is intramuscular.

5. The method of claim 3 wherein injection is intravenous.

6. The method of claim 1 wherein said administering is ingestion.

7. The method of claim 1 wherein identification is achieved by measuring the levels of CA-I, CA-II, CA-III, CA-IV, and CA-VI in the blood of the subject.

8. The method of claim 1 wherein identification is achieved by measuring levels of CA-I, CA-II, CA-III, CA-IV, and CA-VI in biopsied tissues from the subject.

9. The method of claim 1 wherein identification is achieved by measuring levels of CA-I, CA-II, CA-III, CA-IV, and CA-VI in cerebro-spinal fluid of the subject.

\* \* \* \* \*

UNITED STATES PATENT AND TRADEMARK OFFICE
CERTIFICATE OF CORRECTION

PATENT NO. : 6,821,997 B1
DATED : November 23, 2004
INVENTOR(S) : Victorio C. Rodriquez It is certified that error appears in the above-identified patent and that said Letters Patent is hereby corrected as shown below:

Column 6,
Line 33, please delete "claim 1" and insert:
-- 1. A method for the treatment and prophylaxis of conditions of aging associated with a decreased presence of cell-specfic carbonic anhydrase enzymes in the brain, wherein said conditions are selected from the group consisting of chronic neurodegenerative conditions, dementia, Alzheimer's disease, which method comprises:
    identifying one or more cell-specific carbonic anhydrase enzymes that are present at decreased levels in the blood, brain cells or cerebro-spinal fluid of a subject in need of treatment and prophylaxis of said conditions; and
    then administering a pharmaceutically effective, non-toxi amount of a sulfonylamindo derivative of histamine. --

Column 6,
Line 26, after "1" please delete "grain" and insert -- gram --.
Line 46, please delete "claim 2" and insert:
    -- 2. The method of claim 1, wherein said sulfonylamido derivative of histamine, when administered to a human patient, will promote the natural production of the cell-specific enzyme that is present at decreased levels in the subject. --

Signed and Sealed this

Fifth Day of April, 2005

JON W. DUDAS
*Director of the United States Patent and Trademark Office*